United States Patent
Clausi et al.

(10) Patent No.: US 7,081,553 B2
(45) Date of Patent: Jul. 25, 2006

(54) COBALT FLASH PROCESS

(75) Inventors: Dominic T. Clausi, Katy, TX (US); Eddy T. van Driessche, Eeklo (BE); Ronald D. Garton, Baton Rouge, LA (US); James T. Ritchie, Zachary, LA (US); Nico A. de Munck, Barendrecht (NL)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/508,925

(22) PCT Filed: Mar. 28, 2003

(86) PCT No.: PCT/US03/09721

§ 371 (c)(1),
(2), (4) Date: Sep. 24, 2004

(87) PCT Pub. No.: WO03/082788

PCT Pub. Date: Oct. 9, 2003

(65) Prior Publication Data

US 2005/0119508 A1 Jun. 2, 2005

Related U.S. Application Data

(60) Provisional application No. 60/368,891, filed on Mar. 29, 2002.

(51) Int. Cl.
*C07C 45/50* (2006.01)

(52) U.S. Cl. ............ 568/429; 568/444; 568/451; 568/454

(58) Field of Classification Search ............ None
See application file for complete search history.

(56) References Cited

U.S. PATENT DOCUMENTS

| | | | |
|---|---|---|---|
| 2,638,485 A | 5/1953 | Mertzweiler | 260/604 |
| 2,744,936 A | 5/1956 | Mertzweiler | 260/604 |
| 2,754,331 A | 7/1956 | Smith | 260/604 |
| 2,754,332 A | 7/1956 | Mason | 260/604 |
| 2,757,204 A | 7/1956 | Ratcliff | 260/604 |
| 2,757,205 A | 7/1956 | Mertzweiler et al. | 260/604 |
| 2,757,206 A | 7/1956 | Jones et al. | 260/604 |
| 2,767,217 A | 10/1956 | Moise et al. | 260/604 |
| 2,768,974 A | 10/1956 | Krebs et al. | 260/604 |
| 2,812,356 A | 11/1957 | Aldridge et al. | 260/604 |
| 2,816,933 A | 12/1957 | Mertzweiller | 260/638 |
| 2,834,815 A | 5/1958 | Mertzweiller et al. | 260/638 |
| 3,055,942 A | 9/1962 | Roming, Jr. | 260/604 |
| 3,288,857 A | 11/1966 | Kyle et al. | 260/604 |
| 3,725,534 A | 4/1973 | Reisch | 423/417 |
| 3,960,978 A | 6/1976 | Givens et al. | 260/683.15 R |
| 4,021,502 A | 5/1977 | Plank et al. | 260/683.15 R |
| 4,076,842 A | 2/1978 | Plank et al. | 423/328 |
| 4,150,062 A | 4/1979 | Garwood et al. | 260/673 |
| 4,211,640 A | 7/1980 | Garwood et al. | 208/255 |
| 4,520,221 A | 5/1985 | Hsia Chen | 585/517 |
| 4,522,929 A | 6/1985 | Chester et al. | 502/77 |
| 4,524,232 A | 6/1985 | Chester et al. | 585/517 |
| 4,547,613 A | 10/1985 | Garwood et al. | 585/533 |
| 4,568,786 A | 2/1986 | Hsia Chen et al. | 585/517 |
| 4,625,067 A | 11/1986 | Hanin | 568/451 |
| 4,855,527 A | 8/1989 | Page et al. | 585/527 |
| 4,870,038 A | 9/1989 | Page et al. | 502/62 |
| 5,026,933 A | 6/1991 | Blain et al. | 585/7 |
| 5,112,519 A | 5/1992 | Giacobbe et al. | 252/174.21 |
| 5,215,667 A | 6/1993 | Livingston, Jr. et al. | 210/651 |
| 5,235,112 A | 8/1993 | Nadler et al. | 568/451 |
| 5,237,104 A | 8/1993 | Summerlin | 568/451 |
| 5,237,105 A | 8/1993 | Summerlin | 568/451 |
| 5,245,072 A | 9/1993 | Giacobbe et al. | 560/99 |
| 5,336,473 A | 8/1994 | Nadler et al. | 422/193 |
| 5,410,090 A | 4/1995 | Beadle et al. | 568/451 |
| 5,417,869 A | 5/1995 | Giacobbe et al. | 252/33.6 |
| 5,457,240 A | 10/1995 | Beadle et al. | 568/451 |
| 5,985,804 A | 11/1999 | Ashjian et al. | 508/287 |
| 6,013,851 A | 1/2000 | Verrelst et al. | 585/533 |
| 6,015,928 A | 1/2000 | Gubisch et al. | 568/882 |
| 6,150,322 A | 11/2000 | Wright et al. | 514/16 |

FOREIGN PATENT DOCUMENTS

| | | |
|---|---|---|
| GB | 893524 | 4/1962 |
| WO | WO 93/24436 | 12/1993 |
| WO | WO 93/24437 | 12/1993 |

*Primary Examiner*—Sikarl A. Witherspoon
(74) *Attorney, Agent, or Firm*—Andrew B. Griffis

(57) ABSTRACT

The Cobalt Flash Process is modified by replacing formic acid with acetic acid as process acid. Efficiency using acetic acid as process acid is achieved by two improvements which may be added separately and independently: (1) separation of acetic acid and water from the condensate distilled off in the cobalt salt concentration stage; and (2) removal of formic acid from the system by reaction with the product alcohol in the preformer.

20 Claims, No Drawings

COBALT FLASH PROCESS

CROSS REFERENCE TO RELATED APPLICATIONS

This application is a National Stage Application of International Application No. PCT/US03/09721, filed Mar. 28, 2003, which claims the benefit of Provisional Application No. 60/368,891, filed Mar. 29, 2002. These applications are incorporated herein by reference.

FIELD OF THE INVENTION

The invention relates to efficient recycle of acetic acid in the Cobalt Flash Process for the production of alcohols useful in the manufacture of plasticizers, detergents, solvents, synthetic lubricants, and the like.

BACKGROUND

Hydroformylation reactions involve the preparation of oxygenated organic compounds by the reaction of synthesis gas (carbon monoxide and hydrogen) with carbon compounds containing olefinic unsaturation (hereinafter "olefinic material"). The reaction is generally performed in the presence of a hydroformylation catalyst such as cobalt or rhodium, and results in the formation of a product comprising an aldehyde which has one more carbon atom in its molecular structure than the starting olefinic feedstock. By way of example, higher alcohols useful as intermediates in the manufacture of plasticizers, detergents, solvents, synthetic lubricants, and the like, are produced commercially in the so-called Oxo Process (i.e., transition metal catalyzed hydroformylation) by conversion of $C_3$ or higher olefin fractions (typically $C_5$–$C_{12}$) to an aldehyde-containing oxonation product having one additional carbon atom (e.g., $C_6$–$C_{13}$). Hydrogenation and distillation yields the respective alcohols, or the aldehydes may instead be further oxidized to the respective acids.

The Oxo Process to convert olefinic material to aldehydes generally proceeds through three basic stages as explained below by specific reference to a catalyst comprising cobalt.

In the first stage, or oxonation reaction, the olefinic material and the proper proportions of CO and $H_2$ are reacted in the presence of a cobalt-containing carbonylation catalyst to give a product comprising predominantly aldehydes containing one more carbon atom than the reacted olefin. Typically, alcohols, paraffins, acetals, and other species are also produced in the hydroformylation reaction. The catalyst can be supplied to this section by numerous methods known in the art, such as by injecting cobalt acetate (or cobalt formate) directly or by supplying cobalt from a precarbonylation stage or catalyst makeup stage in the form of a cobalt anion ($Co^{-1}$) or organically soluble form of $Co^{+2}$, such as cobalt naphthenate, oleate, or cobalt oxides.

The oxygenated organic mixture from the oxonation (or oxo) reactor(s), which typically contains various salts and molecular complexes of the metal from the catalyst (i.e., the "metal values") as well as the aldehydes, alcohols, acetals and other species, referred to as the crude aldehyde or crude hydroformylation mixture, is treated in a second stage, the demetalling stage. In the demetalling stage, typically a reaction is caused to separate the metal values from the aldehyde, such as by injecting dilute acetic acid. The crude hydroformylation mixture separates into phases with the organic phase comprising the desired aldehyde separated from the aqueous phase comprising cobalt acetate. The organic phase is sent to other unit operations downstream to be converted to the desired final product.

In the third stage of the Oxo Process the metal values removed in the second stage are worked up in a way that they can be reused in the oxonation section. There are several ways taught in the prior art to work up this catalyst. For example, one way is to convert the aqueous metal salt to an organically miscible compound such as cobalt naphthenate, and inject it directly into the oxonation reactor(s). Another way is to subject the aqueous salt solution in the presence of an organic solvent to high pressure synthesis gas, converting it to active carbonyl, and delivering it to the oxonation section via extraction, stripping or the like. It would be ideal if all of the cobalt is recovered and eventually passed in the proper form to the first stage described above.

These aforementioned three process stages may occur in more or less than three distinct vessels and numerous variations and improvements, including adding to, deleting from, or combining these stages, have been proposed over the years with various degrees of success.

U.S. Pat. No. 2,816,933 observes that the most direct method of utilization of cobalt acetate consists of recycling directly the aqueous cobalt stream from the demetalling stage to the primary aldehyde synthesis zone of the oxonation reaction stage. One problem with such a scheme is it introduces considerable quantities of water in to the reactor. Excess water substantially decreases the olefin conversion and may result in reactor flooding and complete loss of reaction. Instead, the patent teaches that after injection of sufficient acetic acid to combine with all the cobalt present in the demetalling stage, the entire mixture, including crude product, is allowed to separate into aldehyde and aqueous phases in a settler. After sufficient time, the lower aqueous phase containing cobalt acetate is passed to an extraction vessel where the cobalt salt is converted into oil soluble form and finally after numerous additional steps is used to supply a portion of the catalyst requirements for the oxonation reaction. Such a procedure is complex and inefficient and adds to the operating cost of the process. In addition, acetic acid is highly soluble in the organic phase and without additional treatment downstream from the demetalling stage, too much acetic acid passes with the aldehyde to the hydrogenation (or hydro) stage. Such "additional treatment", for instance washing with fresh water, is economically and environmentally unattractive.

Numerous other inventions directed to the more efficient use of acetic acid are taught, for instance, in U.S. Pat. Nos. 2,638,485; 2,744,936; 2,754,332; 2,757,204; 2,757,206; 2,768,974; 2,812,356; and 3,055,942.

A major improvement in the oxo process is taught in U.S. Pat. No. 4,625,067. The patent describes recovery of cobalt values by contacting the crude hydroformylation product with a stripping gas to entrain volatile cobalt compounds, in the presence of water or aqueous acid ("Cobalt Flash Process"). A large portion of cobalt values in the form of cobalt carbonyl compounds absorbed into crude aldehyde product is taken overhead in the stripper reactor(s) and returned to the oxo reactor(s) by adsorption into the olefin feed stream. The partially decobalted crude product is then passed to the demetalling reaction and contacted with aqueous acid as in the prior art Oxo Processes. In the Cobalt Flash Process the cobalt-containing aqueous phase is separated and concentrated in an evaporator, while the decobalted organic phase containing crude aldehyde product (or oxo product) is passed to the hydrogenation reaction in the case where alcohol is the desired product or to further oxidation in the case where acid is the desired product.

Here again numerous improvements on the Cobalt Flash Process have been proposed, such as in U.S. Pat. Nos. 5,235,112; 5,237,104; 5,237,105; 5,336,473; 5,410,090; 5,457,240; WO 93/24437; and WO 93/24436.

In the Cobalt Flash Process as currently practiced, after the aqueous phase comprising cobalt formate is separated from the organic phase comprising oxo product in the demetalling reaction, the aqueous phase is passed to an evaporator where cobalt formate is concentrated before being passed to a preformer wherein the aqueous cobalt salt ($Co^{+2}$) is converted to oil soluble $Co^{-1}$ by reaction with carbon monoxide and hydrogen in the presence of an oil phase (commonly an aldehyde or alcohol, such as the product of the oxonation reaction). The cobalt is then passed into the stripper reactors and/or oxonation reactors to supplement the cobalt recovered in the strippers. Additional fresh cobalt catalyst is typically necessary and is added as, for instance, cobalt acetate.

Although the prior art suggests that acetic acid, propionic acid, and the like, may be used in the demetalling stage, numerous patents state that formic acid is preferred (such as the aforementioned U.S. '067 at col. 5, line 55+; U.S. '112 at col. 7, line 55+; U.S. '240 at col. 8, line 15; and U.S. '473 at col. 7, line 63+).

At least part of the reason for the preference of the lower molecular weight organic acid is the lower solubility of formic acid relative to acetic acid in the aldehyde product-containing oil phase separated from the cobalt values in the demetalling reaction. The acetic acid is difficult to remove from the desired product and moreover forms acetate esters with alcohols that are still more difficult to remove.

Moreover, too much acetic acid is lost in the evaporator used to concentrate the cobalt values after the demetalling reaction. Significantly more acetic acid is lost relative in this stage relative to formic acid. This is because acetic acid has the curious property of being more volatile than its lower molecular weight congener, formic acid, at least at low concentrations typically used in the Cobalt Flash Process.

Another reason for the preference of formic acid in practice is that formic acid is a natural by-product of the hydroformylation reaction; thus the loss of formic acid in the demetalling reaction (to aldehyde product contamination) is mitigated to some extent by this by-product production.

However, provided the aforementioned drawbacks could be solved, the use of acetic acid in place of formic acid in the Cobalt Flash Process offers certain benefits relative to formic acid, such as:

formic acid is corrosive to the process equipment, leading to high maintenance costs and low service factors. The replacement of the reactors and other units in the system is extremely expensive. Also, the high corrosive rate results in buildup of corrosive metals in the water, requiring frequent purging and hence loss of cobalt and an addition to the environmental load of the process, which is expensive to mitigate;

the solubility of cobalt in aqueous acetic acid is significantly higher than in aqueous formic acid, thus allowing for greater product throughput, provided, again, that the aforementioned problems could be solved;

the rate of preforming is higher with cobalt acetate as compared with cobalt formate, thus allowing higher flow rate through the preformer.

Accordingly, it would be advantageous to overcome the aforementioned drawbacks associated with the use of acetic acid in the Cobalt Flash Process and replace the formic acid currently used.

SUMMARY OF THE INVENTION

The present invention solves certain technical problems associated with the use of acetic acid in the Cobalt Flash Process, providing an economically and environmentally beneficial improvement to the Cobalt Flash Process.

It has now been found that the aforementioned technical problems associated with the use of acetic acid may be solved by adding the following steps to the Cobalt Flash Process: (1) separating the condensate generated in the evaporator step into an acetic acid-depleted water stream, preferably to be recycled as aldehyde product wash water, and an acetic acid-rich stream, preferably to be recycled as process make-up acid; and (2) controlling the accumulation of formic acid, which originates in the oxonation reactor(s), by flowing an organic stream comprising an alcohol through the preforming section, and allowing the alcohol to selectively react with the formic acid. The resulting formate ester is removed from the system in the demetalling stage due to the formate esters' solubility in the product aldehyde and can be subsequently readily removed from the desired product, such as by decomposition in the hydrogenation stage in the case where the final product is alcohol.

Thus, a principal object of the invention is to avoid the corrosive effects of formic acid in the Cobalt Flash Process by switching to the less corrosive acetic acid, to increase the service life of the equipment while avoiding some of the technical problems associated with acetic acid in prior art processes.

A further object of the invention is to decrease the economically and environmentally unsound waste of process acid by an efficient acetic acid recycle scheme that minimizes buildup of formic acid by-product.

Still a further object of the invention is to provide a cleaner final product at a lower cost by providing a convenient method of washing the aldehyde product of the oxonation reaction with internal process fluids rather than fresh water.

Yet still another object of the invention is to increase cobalt circulation capacity due to the high solubility of cobalt acetate in water relative to cobalt formate.

These and other objects, features, and advantages of the present invention will become apparent as reference is made to the following detailed description, preferred embodiments, specific examples and appended claims.

DETAILED DESCRIPTION

The present invention is an improvement on the Cobalt Flash Process to allow the efficient use of acetic acid instead of formic acid as the process acid.

As used herein, the "Cobalt Flash Process" comprises: (1) reacting synthesis gas with an olefinic material in the presence of a carbonylation catalyst in one or more oxo reactors to produce a crude aldehyde product; (2) passing the crude aldehyde product to one or more stripper reactors where the crude product is contacted with water and synthesis gas (and also typically but optionally acetic acid, as discussed hereinafter); (3) passing the overhead, comprising cobalt carbonyl compounds, from the stripper reactor(s) back to the oxo reactor(s) and passing the bottoms portion, comprising crude aldehyde (or crude oxo or crude hydroformylation; the terms are used synonymously herein) product, from the stripper reactor(s) to one or more demetalling reactor(s), wherein the cobalt values are completely (or nearly so) converted into cobalt acetate in the presence of acetic acid which is added into the stripper(s) or demetalling reactor (or both), e.g., by air oxidation or thermal decomposition; (4) separating the crude oxo product into an aqueous phase, comprising cobalt values, and an organic phase, comprising the hydroformylation product; (5) passing the aforementioned organic phase to be further processed as desired downstream, such as by hydrogenation or oxidation, and passing the aqueous phase comprising cobalt acetate to an evaporator; (6) concentrating the cobalt acetate solution in the evaporator by distilling off water and acetic acid; (7) passing the thus-concentrated cobalt acetate to a preforming stage wherein the cobalt values are contacted with synthesis gas in the presence of an organic phase; (8) recovering or recycling the resulting cobalt carbonyl compounds by passing them through the stripper reactors.

The olefinic material used in step (1), above, may be short or long chained compounds containing olefinic unsaturation, depending on the final product desired. Most organic compounds possessing at least one non-aromatic carbon-carbon double bond may be reacted by this method. Generally the compound will have at least three carbon atoms although hydroformylation using ethylene is known (see, for instance, U.S. Pat. No. 6,150,322). Thus, straight and branched-chained olefins and diolefins such as propylene, butylenes, pentenes, hexenes, heptenes, butadiene, pentadiene, styrene, olefin polymers such as di- and tri-isobutylene and hexene and heptene dimers, olefinic fractions from the hydrocarbon synthesis process, thermal or catalytic cracking operations, and other sources of hydrocarbon fractions containing olefins may be used as starting material, depending upon the nature of the final product desired. The feed may include a mixture of isomers, both skeletal and in double bond location or it may be isomerically pure (or nearly so) skeletally and/or in double bond location.

In a preferred embodiment, the olefinic material is a mixture of olefins having a carbon number of from $C_3$ to $C_{18}$, more preferably $C_5$ to $C_{18}$. It will be recognized that the olefin feed may not consist of 100% olefins within the specified carbon number range, but may be a distribution of olefins having different carbon lengths with at least 50 wt. %, preferably 70 wt. %, more prefereably 80 wt. %, still more preferably 90 wt. % of olefins in the specified carbon number range. In certain cases it may be preferable to use a feed of 100 wt. % (or nearly so) of the specified carbon number or carbon number range.

In another preferred embodiment, the olefinic material is the olefinic reaction product of the acid catalyzed oligomerization of propylene and/or butenes, which may also optionally include pentenes.

In yet another preferred embodiment, the olefinic material is the olefinic reaction product of the oligomerization of various olefins and compounds having olefinic unsaturation, using surface deactivated zeolite catalysts as described in U.S. Pat. Nos. 3,960,978; 4,021,502; 4,076,842; 4,150,062; 4,211,640; 4,520,221; 4,522,929; 4,524,232; 4,547,613; 4,568,786; 4,855,527; 4,870,038; 5,026,933; 5,112,519; 5,245,072; 5,417,869; 5,985,804; and 6,013,851.

Even more preferred as olefinic material in the present invention are $C_6$ to $C_{26}$ olefins, even more preferably $C_9$ to $C_{26}$ olefins, still more preferably $C_9$ to $C_{23}$ olefins, yet still more preferably $C_9$ to $C_{18}$ olefins, prepared by contacting lower olefins under polymerization conditions with siliceous monodimensional acidic zeolites such as ZSM-22 and ZSM-23 zeolite having pore activity and wherein the zeolite surface is rendered substantially inactive for acidic reactions. By "lower olefins" or "lower olefinic material" as used herein is simply meant that the starting material to be oligomerized over the zeolite have less carbon numbers than the final product. The oligomers may be dimers, trimers, tetramers or higher oligomers, or mixtures thereof. It is preferred that the starting material is a $C_3$ or greater olefin (or mixtures thereof), and in a preferred embodiment the olefinic material supplied to the oxonation reactor(s) according to the present invention derive from the oligomerization of $C_3$ and/or $C_4$ olefins using the aforementioned modified zeolites. In a particularly preferred embodiment, a feed is used comprising butenes (still more preferably n-butene) and propylene in the ratio of about 1:0.01 to 1:0.049 wt. %, yet still more preferably along with paraffins to act as a heat sink in the reaction. The amount of paraffins to use can be determined by one of ordinary skill in the art.

Yet still another preferred embodiment is the use of LAOs and/or LIOs (linear alpha olefins and linear internal olefins, respectively), which terms are well-known in the art, as olefinic feed.

Other more preferred olefinic materials used as a feed into the oxonation reactors include oligomers produced by the Octol® process or the Dimersol® process. See, for instance, the previously mentioned U.S. Pat. No. 6,015,928. Yet another more preferred olefinic material includes oligomers produced using solid phosphoric acid (SPA) catalysts and those produced using ZSM-57 catalysts, procedures which are known in the art.

Another more preferred feed comprises 0.1–20 wt. % isoolefin, particularly isobutylene and or isoamylene, more preferably wherein the content of the isobutylene and/or isoamylene is from 0.5–5.0 wt. %. A preferred source of such a feed is the unreacted effluent from an MTBE unit, which is a yet still more preferable embodiment.

Reactor conditions for each stage are well-known in the art and are not critical to achieve the objects of the present invention. Typical hydroformylation reaction conditions include a temperature of about 125° C. to about 200° C., a pressure of about 300 psig to about 1500 psig, and a catalyst to olefin ration of about 1:1000 to about 1:1. The molar ratio of hydrogen to carbon monoxide is usually about 1 to about 10. The process may also be carried out in the presence of an inert solvent such as ketones, e.g, acetone, or aromatic compounds such as benzene, toluene and the xylenes.

One aspect of the present invention is separating the decobalted distillate generated in the evaporator step (step (6) in the Cobalt Flash Process set forth above) into an acetic acid-depleted water stream, preferably to be recycled as aldehyde product wash water as described in more detail below, and an acetic acid-rich stream, preferably to be recycled as process make-up acid, e.g., to the stripper reactor(s) and/or to the demetalling stage.

According to the present invention, the condensate generated from the evaporator overhead distillate is then separated into an acetic acid-rich stream and an acetic acid-depleted stream comprising primarily water. This condensate separation step may be accomplished by, for instance, membrane separation or liquid-liquid extraction (such as with ethyl acetate). Methods of separating aqueous acetic acid into two streams, one rich in acetic acid and one depleted in acetic acid, are known.

It is preferred that membrane separation be used in this step, more preferably reverse osmosis membrane separation. It is still more preferable that a polymeric membrane is used, the most preferred membrane being a membrane comprising an aromatic polyamide. Such systems are commercially available, for instance, from Osmonics, Inc., of Minnetonka, Minn., USA.

In another preferred embodiment, a pervaporation system such as that produced by Sulzer Chemtech GmbH Membrane Systems, Neunkirchen, Germany, can be used. The membrane material here is preferably polymeric or even more preferably ceramic.

The acetic acid-rich portion from the evaporator condensate separation step may then be recycled into the process at any desired point, preferably in the demetalling reactor(s) and/or in the stripper reactor(s).

The acetic acid-depleted water stream can be used as desired. In a preferred embodiment, the acetic acid-depleted water stream from the condensate separation step according to the present invention is used in a wash tower to wash the organic phase containing crude product from the demetalling reactor(s). In this preferred embodiment, decobalted oxonation product from the demetalling reactor(s), which still contains some acetic acid and other water-soluble impurities, is washed with the water from the aforementioned evaporator condensate separation step. The thus-washed oxonation product is passed overhead from the wash tower to the next desired processing step, such as hydrogenation or further oxidation. The wash water, now more concentrated with acetic acid extracted from the organic phase, is taken off as bottoms. This dilute acetic acid may now be used directly in the process as desired, such as in the demetalling reactor and/or in the stripper reactor(s). By this preferred embodiment of using the internal process fluids to wash the organic phase comprising the aldehyde, the purity of the desired product is still more significantly improved and additional economic advantages are achieved by more complete and efficient acetic acid recycle.

Another aspect of the present invention is controlling the accumulation of formic acid by flowing alcohol through the preforming section, and allowing the alcohol to selectively react with the formic acid, whereby the resulting formate ester can be removed from the system in the demetalling stage due to the formate esters' solubility in the product aldehyde. The formate ester can be subsequently removed from the final product, for instance by decomposition during hydrogenation. This aspect of the present invention will be described in more detail below.

When acetic acid is used as process acid in the Cobalt Flash Process according to the present invention, the concentrated cobalt acetate portion from the evaporator is passed to the preformer. In the preformer, cobalt in the form of $Co^{+2}$ is reacted with synthesis gas in the presence of an organic phase comprising an organic alcohol. According to the second aspect of the present invention, the formic acid that is also present in this stream, as a result of the reactions in the oxonation reactor(s), is removed by periodically or continuously flowing an organic alcohol through the preformer. It is important that the preforming organic material have some alcohol functionality so that the formate esters can form, but not too much so that significant quantities of acetate esters are also formed, since acetate esters are difficult to remove from the final product and indeed are believed to be a cause of hydrogenation deactivation under certain conditions. In contrast, formate esters are readily separated, such as by decomposition in the downstream hydrogenation reactor. Fortunately the kinetics favor ester formation with formic acid over acetic acid, so that by controlling the amount of alcohol added and the time in the preformer, a sufficient amount of formic acid can be removed without substantial acetate ester formation. This can be achieved without undue experimentation by one of ordinary skill in the art in the presence of the present disclosure.

The source of the organic alcohol may be, for instance, a portion of the final alcohol produced by hydrogenation of the aldehyde. The organic alcohol may also come from using a portion of the aldehyde product of the oxonation reaction, particularly after it has been washed to remove acetic acid, such as in accordance with the aspect of the present invention discussed previously (i.e., oxonation reaction produces some alcohol, which gets passed through to the organic phase in the wash tower). The actual source of organic alcohol used in the preformer is per se not critical for the purpose of removing formic acid; it may be, for instance, that an alcohol other than product alcohol is preferred, depending on the circumstances. Overall process optimization, however, may depend on using internal process fluids, i.e., wash aldehyde or final product alcohol, as the organic alcohol used in the preformer.

Thus, it is important in this second aspect of the present invention that formate ester formation be maximized while minimizing acetate ester formation to be within an acceptable level in the final product.

The material from the preformer is then passed into the stripper reactor(s) to complete the recycling of the cobalt values. The formate ester formed in the preformer is removed from the system into the organic phase in the demetalling step.

EXAMPLES

The following examples are meant to illustrate the present invention. Numerous modifications and variations are possible and it is to be understood that within the scope of the appended claims, the invention may be practiced otherwise than as specifically described herein.

The prior art Cobalt Flash Process unit was operated using linear $C_9$ olefin feed and using about 1.5 wt. % acetic acid as the process acid. Overall acid loss rate is approximately 250–300 lbs/hr of acetic acid, compared to 50 lbs/hr of formic acid lost during baseline formic acid operations using the same concentration of acid in water. The acetic acid in the overhead from the evaporator contained about 5.5 wt. % acetic acid, compared to about 0.1 wt. % formic acid in the case where the latter is used as process acid. The final $C_{10}$ alcohol product recovered after hydrogenation contained about 2 wt. % acetate ester; typically no more than 0.5 wt % acetate ester is considered acceptable. An acceptable level is readily achieved using formic acid as process acid in the prior art Cobalt Flash Process.

The same Cobalt Flash Process unit is modified and operated according to the present invention using acetic acid as process acid, as detailed below. The modified unit is operated using the same linear $C_9$ olefin feed as above and using about 11 wt. % acetic acid as process acid, allowing about 2–5 times more cobalt loading than allowed by the use of formic acid as process acid. The unit component parts are otherwise operated under the same conditions as in the comparative experiment above, e.g., the oxonation unit and stripper reactor temperature and pressures are within the typical ranges set forth above.

Acetic acid is added to the stripper reactor in the Cobalt Flash Process to convert the cobalt catalyst to cobalt acetate. This stream is then water washed and sent to a settling drum for the aqueous phase, comprising the cobalt values, and the organic phase, comprising the oxo aldehyde product, to separate, as in the prior art process using formic acid.

The aqueous solution comprising acetic acid and cobalt acetate is passed to the evaporator operating at conditions sufficient to cause water to distill overhead. A portion of acetic acid also distills over. The concentrated cobalt acetate portion is taken as the bottom fraction from the evaporator and this concentrated cobalt acetate is passed to the preformer.

The overhead distillate from the evaporator is condensed and passed through a reverse osmosis system including a polymeric membrane comprising an aromatic polyamide. A commercially available system from Osmonics, Inc., is used. In this case the overheads from the evaporator comprised 5.5 wt. % acetic acid. This stream is separated into a concentrated acetic acid stream and an acetic acid-depleted water stream in a 2-pass reverse osmosis system. The first pass comprises of 5 housings, arranged so that the stream is first passed through 2 parallel housings and then combined and passed through three housings in series (i.e., a 2-1-1-1 array). Each of the housings contain 6 Model AD4040 elements supplied by Osmonics, Inc., for a total of 30 elements. The first pass is operated at 1200 psig and 25° C. A small balance tank is placed between the first and second pass. The second pass comprises 2 housings in series, each containing 6 Model AD4040 elements, totaling 12 elements. The second pass is operated at 900 psig and 25° C. This system produces a 0.3 wt % acetic acid-depleted water stream (or "permeate" stream) at 7.2 gallon per minute (gpm) and a 2.8 gpm acetic acid concentrate stream with 18 wt % acetic acid.

The permeate stream is then used to wash the crude aldehyde from the demetalling stage in a 5-stage wash tower. The acetic acid-rich stream is recycled to the stripper reactor.

A portion of $C_{10}$ alcohol product is then metered into the preformer in an amount estimated to maximize formate ester formation and minimized acetate ester formation and mixed with synthesis gas and with the concentrated aqueous cobalt acetate solution taken off as bottoms from the evaporator. This stream is then passed, after about an hour residence time in the preformer, to the stripper reactor and thus recycled back into the system.

The $C_{10}$ alcohol finish product contains acetic acid levels which are within specification (<0.5 wt. %). Acetic acid losses are comparable to those in the prior art Cobalt Flash Process unmodified by the present invention. It is very surprising and unexpected that the use of acetic acid did not deactivate the hydrogenation unit, particularly considering the much higher loadings of acetic acid used in this example according to the present invention, when compared to the loading using formic acid allowed by the prior art Cobalt Flash Process.

Accordingly, the present invention clearly solves technical problems associated with the use of acetic acid in the Cobalt Flash Process and allows for the replacement of formic acid in the prior art process. It thus achieves at least two advantages, which are (1) avoiding the corrosive effects of formic acid on the process reactors, and (2) providing for increased cobalt capacity by higher solubility of cobalt acetate over cobalt formate.

As previously mentioned, the aldehyde product typically is processed downstream, such as by hydrogenation and distillation to alcohol or by further oxidation to acid. These products may also be further processed to more valuable species. For instance, it is particularly beneficial to esterify the alcohols produced according to the present invention for synthetic lubricant and plasticizer end uses. Alcohol ethoxylates from alcohols made according to the present invention, as well as the sulfonated alcohols, are valuable in the surfactant market, particularly in detergents.

While the invention has been described by specific examples and preferred embodiments, there is no intent to limit the spirit of the inventive concept by such examples and preferred embodiments. Moreover, it is to be noted that all patents cited herein are incorporated herein by reference.

Accordingly, the preferred embodiments include:

in the hydroformylation of olefins by the Cobalt Flash Process, wherein an olefinic material is contacted with synthesis gas in the presence of a cobalt hydroformylation catalyst to produce an aldehyde product containing one more carbon atom than the olefinic material, the improvement comprising using acetic acid as the process acid and adding at least one additional process step to said Cobalt Flash Process selected from: (1) separating an aqueous acetic acid distillate from an evaporator, used after a demetalling stage, into a concentrated acetic acid stream and an acetic acid-depleted water stream, and using the acetic acid-depleted water stream to wash an organic phase comprising crude aldehyde product from the demetalling reactor; and (2) adding an organic alcohol to a preformer reactor whereby formic acid present in said preformer are converted to the corresponding formate ester of the organic alcohol; and also, a process for making an aldehyde by hydroformylation comprising:

contacting synthesis gas with an olefinic organic compound in the presence of a cobalt carbonylation catalyst in one or more oxo reactors to produce a crude product comprising an aldehyde;

passing a crude product produced in said one or more oxo reactors to one or more stripper reactors where the crude product is contacted with water, acid, and synthesis gas, wherein cobalt carbonyl is taken off overhead of said stripper reactors and crude aldehyde is taken of at the bottom portion of said stripper reactors;

passing the portion taken overhead, comprising cobalt carbonyl, from the one or more stripper reactors back to the one or more oxo reactors and passing the bottom portion, comprising crude hydroformylation product and cobalt values, from the one or more stripper reactors to one or more demetalling reactors, wherein the cobalt values are converted into cobalt acetate;

separating the crude hydroformylation into an aqueous phase, comprising cobalt acetate, and an organic phase, comprising the crude hydroformylation product;

recovering the aldehyde phase and passing the aqueous phase to an evaporator;

concentrating the aqueous phase comprising cobalt acetate in said evaporator by distilling off a stream comprising water and acetic acid and taking a bottom portion comprising cobalt acetate from said evaporator comprising concentrated cobalt acetate;

passing said concentrated cobalt acetate to a preforming stage wherein said portion comprising concentrated cobalt acetate values is contacted with synthesis gas in the presence of an organic phase to form cobalt carbonyl;

passing said cobalt carbonyl from the preformer to said one or more stripper reactors;

wherein said process further comprises at least one additional step selected from:

separating said stream comprising water and acetic acid from said evaporator into an acetic acid-rich stream and acetic acid-depleted water stream and using the acetic acid-depleted water stream to wash said aldehyde phase recovered in step (e) in a wash tower, whereby an acetic acid-depleted aldehyde phase is obtained; and adding an organic alcohol to said preforming stage in an amount and for a time sufficient to convert a substantial portion of formic acid impurities into formate esters of said organic alcohol while avoiding a substantial portion of acetic acid conversion to acetate esters of said organic alcohol;

and also more preferred embodiments including modifying either one or both of the aforementioned preferred embodiments modified by one or more of the following still more preferred embodiments:

wherein both additional process steps are used; wherein the separating is by reverse osmosis using a polymeric membrane comprising an aromatic polyamide; wherein the separating is by pervaporation using a ceramic membrane; wherein the organic alcohol added to said preformer is provided by recycling a portion of the aldehyde washed with said acetic acid-depleted water stream; or wherein the process further comprises a step of hydrogenating said aldehyde to an alcohol and wherein a portion of said alcohol is recycled to said preformer; or wherein the olefinic material that is hydroformylated is made by oligomerizing a lower olefinic material over a siliceous acidic monodimensional zeolite selected from ZSM-22 and ZSM-23 having acidic pore activity and wherein the zeolite surface is rendered substantially inactive for acidic reactions with 2,4,6-collidine,; or wherein said lower olefinic material is provided by n-butene and propylene in the ratio of about 1:0.01 to 1:0.49; or wherein the olefinic material that is hydroformylated is made by a process selected from the Octol® process, the Dimersol® process, an oligomerization process using a solid phosphoric acid catalyst, and an oligomerization process using ZSM-57.

What is claimed is:

1. In the hydroformylation of olefins by the Cobalt Flash Process, wherein an olefinic material is contacted with synthesis gas in the presence of a cobalt hydroformylation catalyst to produce an aldehyde product containing one more carbon atom than the olefinic material, the improvement comprising using acetic acid as the process acid and separating an aqueous acetic acid distillate from an evaporator, used after a demetalling stage, into a concentrated acetic acid stream and an acetic acid-depleted water stream, and using the acetic acid-depleted water stream to wash an organic phase comprising crude aldehyde product from the demetalling reactor.

2. The process according to claim 1, the improvement further comprising adding an organic alcohol to a preformer reactor whereby formic acid present in said preformer are converted to the corresponding formate ester of the organic alcohol.

3. The process according to claim 2, wherein said separating is by reverse osmosis using a polymeric membrane comprising an aromatic polyamide.

4. The process according to claim 2, wherein said separating is by pervaporation using a ceramic membrane.

5. The process according to claim 2, wherein the organic alcohol added to said preformer is provided by recycling a portion of the aldehyde washed with said acetic acid-depleted water stream.

6. The process according to claim 2, further comprising a step of hydrogenating said aldehyde to an alcohol and wherein a portion of said alcohol is recycled to said preformer.

7. The process according to claim 1, wherein the olefinic material that is hydroformylated is made by oligomerizing a lower olefinic material over a siliceous acidic monodimensional zeolite selected from ZSM-22 and ZSM-23 having acidic pore activity and wherein the zeolite surface is rendered substantially inactive for acidic reactions with 2,4,6-collidine.

8. The process according to claim 7, wherein said lower olefinic material is provided by n-butene and propylene in the ratio of about 1:0.01 to 1:0.49.

9. The process according to claim 1, wherein the olefinic material that is hydroformylated is made by a process selected from an oligomerization process using a solid phosphoric acid catalyst, and an oligomerization process using ZSM-57.

10. A process for making an aldehyde by hydroformylation comprising:
   (a) contacting synthesis gas with an olefinic organic compound in the presence of a cobalt carbonylation catalyst in one or more oxo reactors to produce a crude product comprising an aldehyde;
   (b) passing a crude product produced in said one or more oxo reactors to one or more stripper reactors where the crude product is contacted with water, acid, and synthesis gas, wherein cobalt carbonyl is taken off overhead of said stripper reactors and crude aldehyde is taken of at the bottom portion of said stripper reactors;
   (c) passing the portion taken overhead, comprising cobalt carbonyl, from the one or more stripper reactors back to the one or more oxo reactors and passing the bottom portion, comprising crude hydroformylation product and cobalt values, from the one or more stripper reactors to one or more demetalling reactors, wherein the cobalt values are converted into cobalt acetate;
   (d) separating the crude hydroformylation into an aqueous phase, comprising cobalt acetate, and an organic phase, comprising the crude hydroformylation product;
   (e) recovering the aldehyde phase and passing the aqueous phase to an evaporator;
   (f) concentrating the aqueous phase comprising cobalt acetate in said evaporator by distilling off a stream comprising water and acetic acid and taking a bottom portion comprising cobalt acetate from said evaporator comprising concentrated cobalt acetate;
   (g) passing said concentrated cobalt acetate to a preforming stage wherein said portion comprising concentrated cobalt acetate values is contacted with synthesis gas in the presence of an organic phase to form cobalt carbonyl;
   (h) passing said cobalt carbonyl from the preformer to said one or more stripper reactors;
   wherein said process further comprises:
   separating said stream comprising water and acetic acid from said evaporator into an acetic acid-rich stream and acetic acid-depleted water stream and using the acetic acid-depleted water stream to wash said aldehyde phase recovered in step (e) in a wash tower, whereby an acetic acid-depleted aldehyde phase is obtained.

11. The process according to claim 10, further characterized by adding an organic alcohol to said preforming stage in an amount and for a time sufficient to convert a substantial portion of formic acid impurities into formate esters of said organic alcohol while avoiding a substantial portion of acetic acid conversion to acetate esters of said organic alcohol.

12. The process according to claim 11, wherein said separating of said stream comprising water and acetic acid is by reverse osmosis using a polymeric membrane comprising an aromatic polyamide.

13. The process according to claim 11, wherein said separating of said stream comprising water and acetic acid is by pervaporation using a ceramic membrane.

14. The process according to claim 11, wherein the organic alcohol added to said preformer is provided by recycling a portion of the aldehyde washed with said acetic acid-depleted water stream.

15. The process according to claim 11, further comprising a step of hydrogenating said aldehyde to an alcohol and wherein a portion of said alcohol is recycled to said preformer.

16. The process according to claim 11, wherein the olefinic material that is hydroformylated is made by oligomerizing a lower olefinic material over a siliceous acidic monodimensional zeolite selected from ZSM-22 and ZSM-23 having acidic pore activity and wherein the zeolite surface is rendered substantially inactive for acidic reactions with 2,4,6-collidine.

17. The process according to claim 16, wherein said lower olefinic material is provided by n-butene and propylene in the ratio of about 1:0.01 to 1:0.49.

18. The process according to claim 11, wherein the olefinic material that is hydroformylated is made by a process selected from an oligomerization process using a solid phosphoric acid catalyst, and an oligomerization process using ZSM-57.

19. The process according to claim 1, wherein the olefinic material that is hydroformylated is made by an oligomerization process using ZSM-57.

20. The process according to claim 11, wherein the olefinic material that is hydroformylated is made by an oligomerization process using ZSM-57.

* * * * *